(12) United States Patent
Betancourt et al.

(10) Patent No.: US 8,323,984 B2
(45) Date of Patent: Dec. 4, 2012

(54) METHOD AND APPARATUS FOR MIXING BLOOD SAMPLES FOR CELL ANALYSIS

(75) Inventors: Tomas Betancourt, Miami, FL (US); Santos E. Vargas, Miami Lakes, FL (US); William Weigong Li, Miami, FL (US); Rongchang Xin, Miami, FL (US)

(73) Assignee: Beckman Coulter, Inc., Brea, CA (US)

( * ) Notice: Subject to any disclaimer, the term of this patent is extended or adjusted under 35 U.S.C. 154(b) by 2552 days.

(21) Appl. No.: 10/324,386

(22) Filed: Dec. 19, 2002

(65) Prior Publication Data

US 2004/0121484 A1    Jun. 24, 2004

(51) Int. Cl.
*G01N 1/38* (2006.01)
(52) U.S. Cl. .............. 436/174; 436/63; 366/101
(58) Field of Classification Search ........... 436/63, 436/66, 68, 69, 174, 179; 366/101, 106, 366/107
See application file for complete search history.

(56) References Cited

U.S. PATENT DOCUMENTS

| | | | |
|---|---|---|---|
| 2,935,840 A | | 5/1960 | Schoppe |
| 2,990,339 A | | 6/1961 | Frank et al. |
| 3,398,935 A | * | 8/1968 | Livesey et al. .............. 366/101 |
| 3,588,053 A | | 6/1971 | Rothermel |
| 3,854,703 A | * | 12/1974 | Gibbs et al. ................ 436/44 |
| 4,136,970 A | | 1/1979 | Cabrera et al. |
| 4,533,255 A | * | 8/1985 | Gronholz et al. ............ 366/108 |
| 4,664,526 A | | 5/1987 | Scheffler et al. |
| 4,674,888 A | | 6/1987 | Carlson |
| 4,815,978 A | | 3/1989 | Mazza et al. |
| 4,845,025 A | * | 7/1989 | Lary et al. ................ 435/2 |
| 4,871,682 A | * | 10/1989 | Mazza .................... 436/179 |
| 5,125,737 A | | 6/1992 | Rodriguez et al. |
| 5,138,181 A | | 8/1992 | Lefevre et al. |
| 5,362,147 A | * | 11/1994 | Schels et al. ............. 366/107 |
| 5,642,937 A | | 7/1997 | Kuan |
| 5,780,306 A | | 7/1998 | Schels et al. |
| 6,074,085 A | | 6/2000 | Scarpa et al. |

FOREIGN PATENT DOCUMENTS

WO    WO 85/03571    *    8/1985

* cited by examiner

*Primary Examiner* — Jan Ludlow
(74) *Attorney, Agent, or Firm* — Warren W. Kurz; Michael L. Bell

(57) ABSTRACT

A method for preparing a volume of blood for cellular analysis in a hematology instrument includes the step of gently mixing the blood sample with a reagent and/or diluent using a stream of air. Preferably, the air stream is directed at the liquid(s) to be mixed at a relatively steep angle, preferably less than about 10 degrees from the normal to the liquid surface. A mixing vessel adapted for use in a hematology instrument for carrying out the method of the invention comprises a cap that supports an air jet for directing the air stream at an angle in keeping with the method of the invention.

9 Claims, 5 Drawing Sheets

METHOD AND APPARATUS FOR MIXING BLOOD SAMPLES FOR CELL ANALYSIS

BACKGROUND OF THE INVENTION

1. Field of the Invention

This invention relates to the field of hematology and, more particularly, to methods and apparatus for preparing blood samples for cell analysis. More specifically, it relates to improvements in methods and apparatus for gently mixing whole blood with diluents and/or reagents (e.g. lytic reagents and stains) to facilitate the detection, differentiation and counting of different cell types in a whole blood sample.

2. Discussion of Prior Art

A thorough analysis of a whole blood sample is commonly effected by examining both the chemical composition of the blood and its cellular makeup. In analyzing the chemistry of blood, a blood sample is first "spun down" with a centrifuge or the like, thereby physically separating the blood cells from the serum in which the cells are normally suspended. The serum, which is the subject of a blood chemistry analysis, is then delivered to an automated clinical chemistry analyzer. The latter initially operates to dispense relatively small volumes of the serum into a plurality of open cuvettes that either already contain, or shortly thereafter receive, specific reagents that facilitate the detection of a particular chemical element, compound, enzyme, etc., of interest in the blood sample. Prior to being analyzed for a characteristic of interest, the blood sample and reagent are thoroughly mixed together to provide a homogeneous mixture, as required for the chemical analysis. For several reasons, not the least of which is to provide a relatively fast cycle time, the mixing process is usually vigorous, sometimes being effected by shooting the reagent liquid into the serum-containing cuvette under pressure, or by using ultrasonic vibrating techniques. The former approach is useful when a relatively large volume of reagent is to be mixed with the blood sample. An alternative mixing scheme is disclosed in U.S. Pat. No. 4,815,978 to Mazza et al. where mixing biological liquids (including blood serum) with reagents and/or diluents in an open-mouth cuvette is achieved by an air jet that operates from a distance to direct a stream of pressurized air at the liquid surface within the cuvette. To achieve optimum mixing, the air jet is directed at a point adjacent the junction of the liquid surface and the cuvette wall. Further, the air jet is inclined so that the angle of incidence made by the air stream and the liquid surface is relatively shallow, whereby a vortex is produced at which the different materials to be mixed are caused to converge and thoroughly mix together. The patent disclosure notes the desirability of maximizing the horizontal component of the air jet, i.e., inclining the air jet more nearly to the liquid surface. In a preferred embodiment, the acute angle at which the air jet attacks the liquid surface is between 8 and 15 degrees measured with respect to horizontal, i.e., the surface of the liquid within the cuvette.

In the field of hematology where the cellular make-up of a blood sample is determined, the process of preparing the sample for analysis is considerably, and necessarily, different from that used in clinical chemistry. In a hematology instrument, the whole blood sample itself is prepared for analysis, not merely the serum. In mixing the whole blood sample with the diluents and/or reagents by which the various different cells can be readily differentiated from other cell types in the sample, it is paramount that the integrity, and especially the morphology, of the cells be preserved. By preserving the integrity of the cells, each cell can be readily distinguishable from other types of cells in the sample on the basis of its physical size (volume), its light-reflecting characteristics, its RF conductivity, and any other parameter by which blood cells can be differentiated from other cell types in the sample. This requirement of preserving the cell integrity dictates a much more gentle mixing process than that used, or proposed for use, in mixing the sample serum with reagents in blood chemistry analyzers. A gentle mixing is especially important when the blood sample is mixed with relatively aggressive reagents, such as lytic reagents, that operate to attack and eliminate certain types of cells (e.g., red cells) so that other cells (e.g., white cells) can be more easily detected and counted. Thus, in hematology instruments designed to automatically differentiate and enumerate various different cell types in a blood sample, it is common employ motor-driven devices, such as orbital mixers and rotating paddles to impart a relatively slow circular motion to the sample-containing reaction vessel, a motion that mimics the gentle orbital mixing movement that can be provided by the human hand. Alternatively, motor-driven rockers or vibrators have been used to gently mix blood samples hematological analysis. While such conventional mixing devices have proven highly effective in producing good sample mixing with minimum damage or alteration to the blood cells, such motor-driven devices may be considered disadvantageous from a number of standpoints. First, they are relatively expensive to manufacture and calibrate. Second, the electric motor used to drive each device tends to introduce both electrical and audio noise that is either detrimental to the instrument performance or unpleasant to the instrument operator. Third, owing to their size and position within the instrument, such devices are relatively costly to maintain and replace.

SUMMARY OF THE INVENTION

In view of the foregoing discussion, it is an object of this invention is to provide an improved method for mixing whole blood with diluent and/or reagent material to provide a homogeneous mixture that is suitable for cellular analysis.

Another object of the invention to provide a less problematic, but equally or even more effective, mixing apparatus for preparing whole blood samples for cellular analysis in a hematology instrument or the like.

According to the invention, it has been unexpectedly found that the air jet-mixing approach disclosed for use in mixing serum with reagents and diluents can, when appropriately modified, be used to homogeneously mix whole blood with reagent materials and/or diluents without adversely affecting the integrity of the blood cells in the sample. Thus, in accordance with a first aspect of the invention, a method for preparing a sample of whole blood for cell analysis in a hematology instrument comprises the steps of dispensing predetermined volumes of whole blood and reagent material in a mixing chamber; and mixing the volumes together by injecting a stream of air under pressure at the top surface of the contained volumes for a time sufficient to produce a homogeneous mixture. Unlike the above-noted air jet mixing proposed for a blood chemistry system in which a relatively strong air stream impinges the liquid at a relatively shallow angle to produce a turbulent mixing vortex, the air stream used by the method of the invention is applied at a relatively low pressure, preferably less than 10 pounds per square inch, and is directed at the liquid surface at a considerably steeper angle, substantially vertical in some cases, whereby a stirring (swirling) and/or a tumbling movement of the miscible liquids (sample and reagents/diluents) is produced. Preferably, the desired motion is achieved by directing the air stream at the liquid surface at an angle of between 0 and about 12 degrees, measured with respect to a normal to the liquid surface, and at a region offset from the center of the mixing chamber. Also preferred is that the air stream is applied from a distance of between about 5 and 20 mm. above the liquid surface. According to a particularly preferred embodiment, the stirring motion is achieved by directing the air stream at the top surface of the contained liquid(s) so that the center of the air stream impacts the liquid surface at a first angle of less than about 8 degrees, measured with respect to a normal to such surface passing through the point of such impact and in a plane perpendicular to a radial plane containing such normal; and the desired tumbling motion is achieved by directing the air stream at the liquid surface at a second angle of not greater than about 4 degrees measured with respect to the aforementioned normal to the liquid surface and in a plane perpendicular to the plane in which the first angle is measured, i.e., in a radial plane.

According to a second aspect of the invention, an improved mixing vessel is provided for receiving a whole blood sample that is to be mixed with another substance to provide a substantially homogeneous mixture useful for blood cell analysis. Such vessel comprises a cup portion comprising a housing defining a mixing chamber, such cup portion having a discharge port through which a liquid mixture within the mixing chamber can be extracted therefrom; and a cap portion sealable with the cup portion housing to enclose the mixing chamber. The cap portion is provided with one or more ports for admitting liquid and other substances to the mixing chamber for mixing, and an additional port for supporting a rectilinear tube through which a jet of air can be directed at the surface of liquid and other substances contained by said mixing chamber for the purpose of mixing said substances. According to a preferred embodiment, the additional port extends at two different angles that are measured with respect to a normal to the liquid surface and in two mutually perpendicular planes.

The invention will be better understood from the ensuing detailed description of preferred embodiments, reference being made to the accompanying drawings in which like reference characters denote like parts.

DETAILED DESCRIPTION OF PREFERRED EMBODIMENTS

Figure 1A:
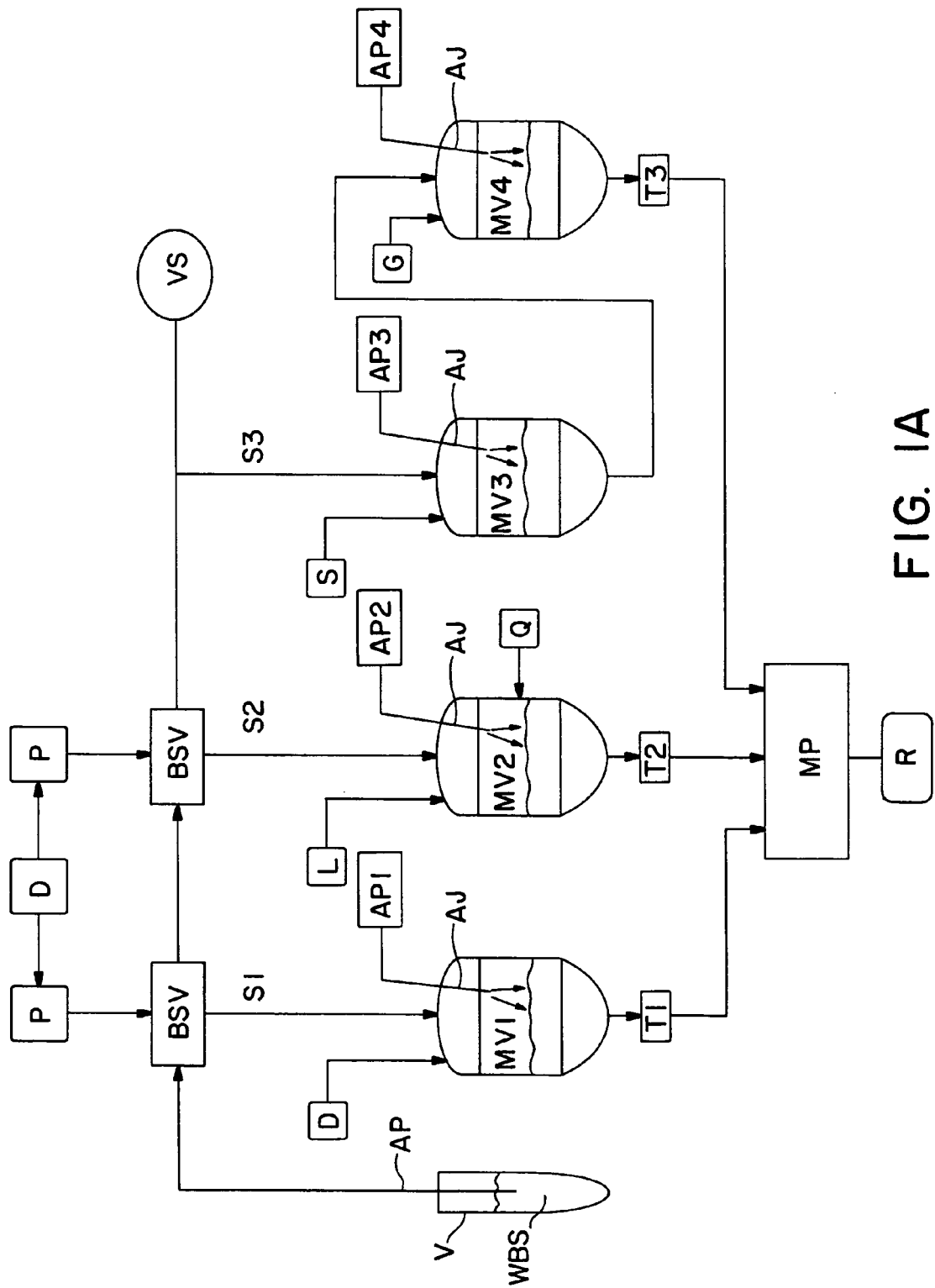
FIGS. 1A and 1B are schematic illustrations of hematology instruments embodying the present invention.
Figure 1B:
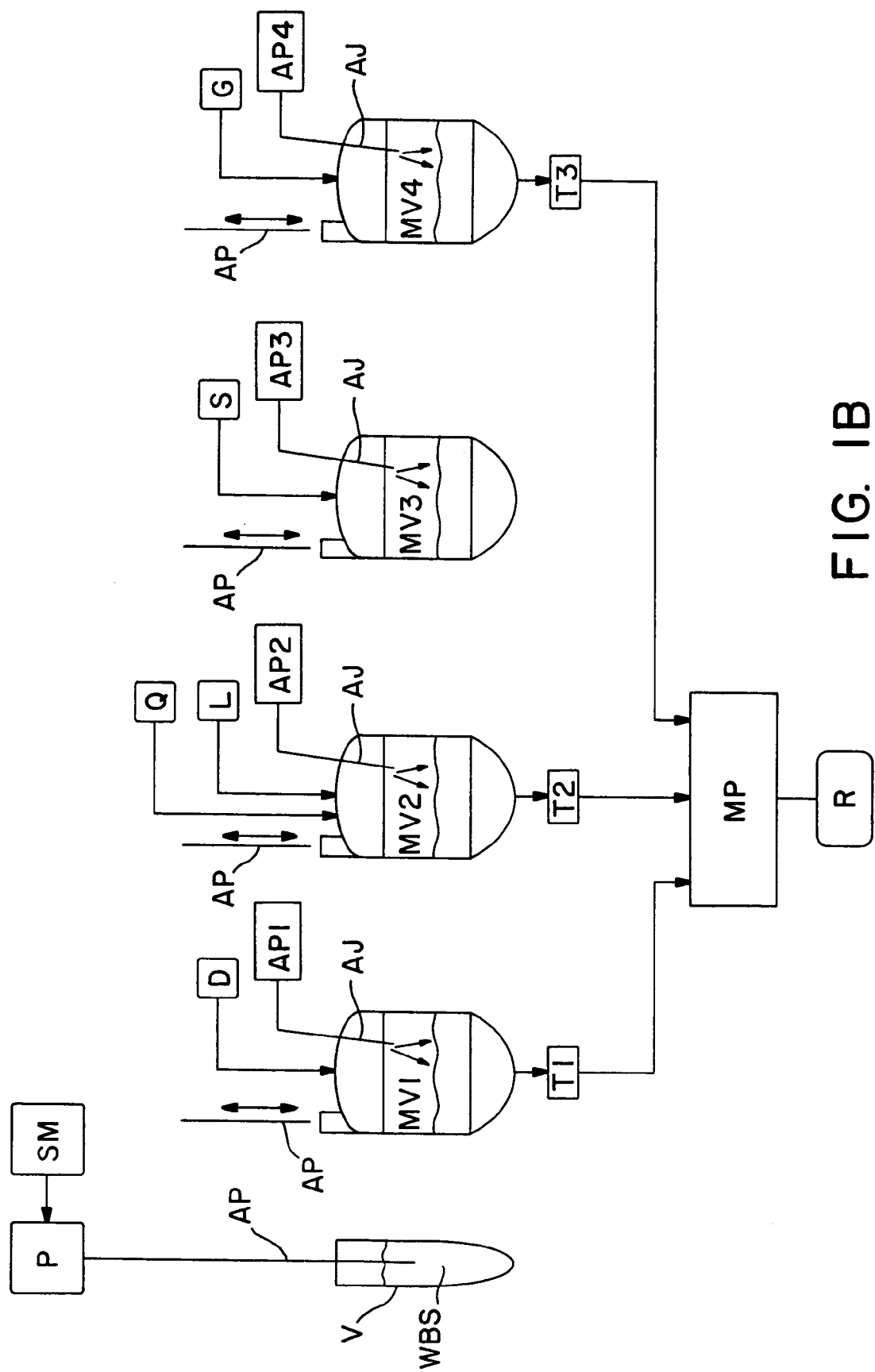

Referring now to the drawings, FIGS. 1A and 1B schematically illustrate two different hematology instruments of the type in which the invention has utility. Such instruments are designed to analyze, in a conventional manner, a whole blood sample WBS for the purpose of ascertaining its cellular makeup. The two instruments differ only in the manner in which they provide metered amounts of whole blood sample to the various mixing vessels MV for preparation for analysis. In the instrument illustrated in FIG. 1A, a vacuum source VS is selectively applied to an aspirating probe AP for the purpose of aspirating a portion of the sample from a vial V. As the sample is aspirated, it is drawn into one or more blood-sampling valves BSV that serve to precisely define and segment the sample volumes that are to be dispensed to the mixing vessels. Thereafter, the instrument operates to dispense precise volumes of the aspirated sample into a plurality of mixing vessels MV1-MV3 to prepare the sample for cellular analysis. One or more pumps P operate to advance a diluent D through the blood sampling valve(s) to urge the segmented and metered sample volumes to the mixing vessels. In the instrument illustrated in FIG. 1B, the vacuum (or pressure) applied to the aspirating probe AP is controlled pump that is driven by a bi-directional stepper motor SM. By applying a predetermined number of vacuum-applying steps to the aspirating probe, the stepper motor serves to precisely meter the volume of sample drawn into the aspirating probe housing. The aspirating probe is then physically moved into and out of each of the respective sample-entrance ports of the mixing vessels and, while positioned within such ports, and the stepper motor is operated in a reverse mode to dispense precise increments of the aspirated sample into the mixing vessels.

In the instruments shown in FIG. 1A, mixing chamber MV1 is used to mix a metered portion S1 of the blood sample with a metered amount of diluent D to provide a relatively diluted blood sample that is suited for subsequent red cell and platelet detection and counting. A portion of the diluted sample is then transported to a first transducer T1, which is typically a conventional impedance transducer. Such a transducer operates to sense the volume or size of blood cells passing through a restricted aperture by monitoring changes in an electrical current that passes through the aperture simultaneously with the cells. Mixing vessel MV2 is used to mix a metered portion S2 of the whole blood sample with a metered amount of lytic reagent or lyse L. The latter serves, in a well known manner, to effectively eliminate red cells from the blood sample, leaving behind the white cells for counting and differentiation. Upon ridding the sample of red cells, the effect of the lytic reagent is quenched by mixing the lysed sample with a quenching reagent Q. A portion of the resulting mixture is then transported to a second transducer T2 for cell detection, differentiation and counting. Transducer T2 may comprise, for example, a conventional optical flow cell designed to simultaneously measure the light-scattering, DC volume and RF conductivity properties of each cell passing through it. Such a flow cell is disclosed, for example, in the commonly assigned U.S. Pat. No. 5,125,737 to Rodriguez et al. The output of transducer T2 is often used to differentiate nucleated red cells, as well as the five major sub-classes of white cells (i.e., lymphocytes, monocytes, eosinophils, neutrophils and basophils). Mixing vessel MV3 may be used for reticulocyte analysis. In it, a metered portion S3 of the whole blood sample is mixed first with a stain S (e.g., new methylene blue stain) that acts to selectively stain the reticulocyte component of the sample. A portion of the stained sample is then incubated and transported to another mixing vessel MV4 where it is mixed with a ghosting reagent G that operates to selectively leak hemoglobin from the red cells and thereby alter their light-reflecting characteristics vis-à-vis the stained retics. A sample of the stained and ghosted mixture from vessel MV4 is then passed through a third transducer T3, another optical flow cell, that is adapted to sense the size, conductivity and light-scattering characteristics of each cell for the purpose of differentiating reticulocytes. The respective outputs of transducers T1-T3 are processed by a suitably programmed microprocessor MP which, in turn, provides a report R listing the cellular characteristics of the processed blood sample. Note, in the instrument of FIG. 1B, the aspirating probe is flushed out after dispensing the metered sample into mixing vessel MV3. The aspirating probe is then used again to aspirate the stained sample from mixing vessel MV3 and to transport it to vessel MV4 for dispensing.

As noted above, in performing a hematological analysis of a blood sample in an instrument as described above, it necessary to provide a homogeneous mixture of the blood sample and reagent to the various transducers for testing. Further, in mixing the blood sample with the reagent and/or a suitable diluent for the blood sample, it is paramount that the mixing process not substantially affect the integrity of the cellular material in the sample.

With the above requirements in mind, the hematology instruments of FIGS. 1A and 1B are shown to further comprise one or more sources of air pressure AP that can be selectively applied to an air jet AJ carried by the cap portion of each of the mixing vessels MV1-MV4. Compared to the air pressure used in mixing blood serums with reagents for the purpose of performing a blood chemistry analysis, the air pressure applied to the air jets AJ is considerably lower, preferably being between only about 2 and 10 pounds per square inch, and more preferably between 3 and 6 PSI. The maximum air pressure chosen is such as to avoid any splashing of the blood mixture in the mixing vessel, which can lead to a loss of cells for analysis, and to avoid any damage or distortion of the cells in the sample which could lead to an improper identification of the blood cells. The avoidance of any splashing and damage or distortion of cells is particularly important in the analysis and differentiation of white cells in the blood sample, since such cells are far less plentiful than red cells in the sample and are more susceptible to damage by any mixing process. The minimum air pressure applied to the air jet is that required to produce the necessary mixing in a reasonable time period, e.g. in a period of between 2 and 10 seconds.

Figure 2:
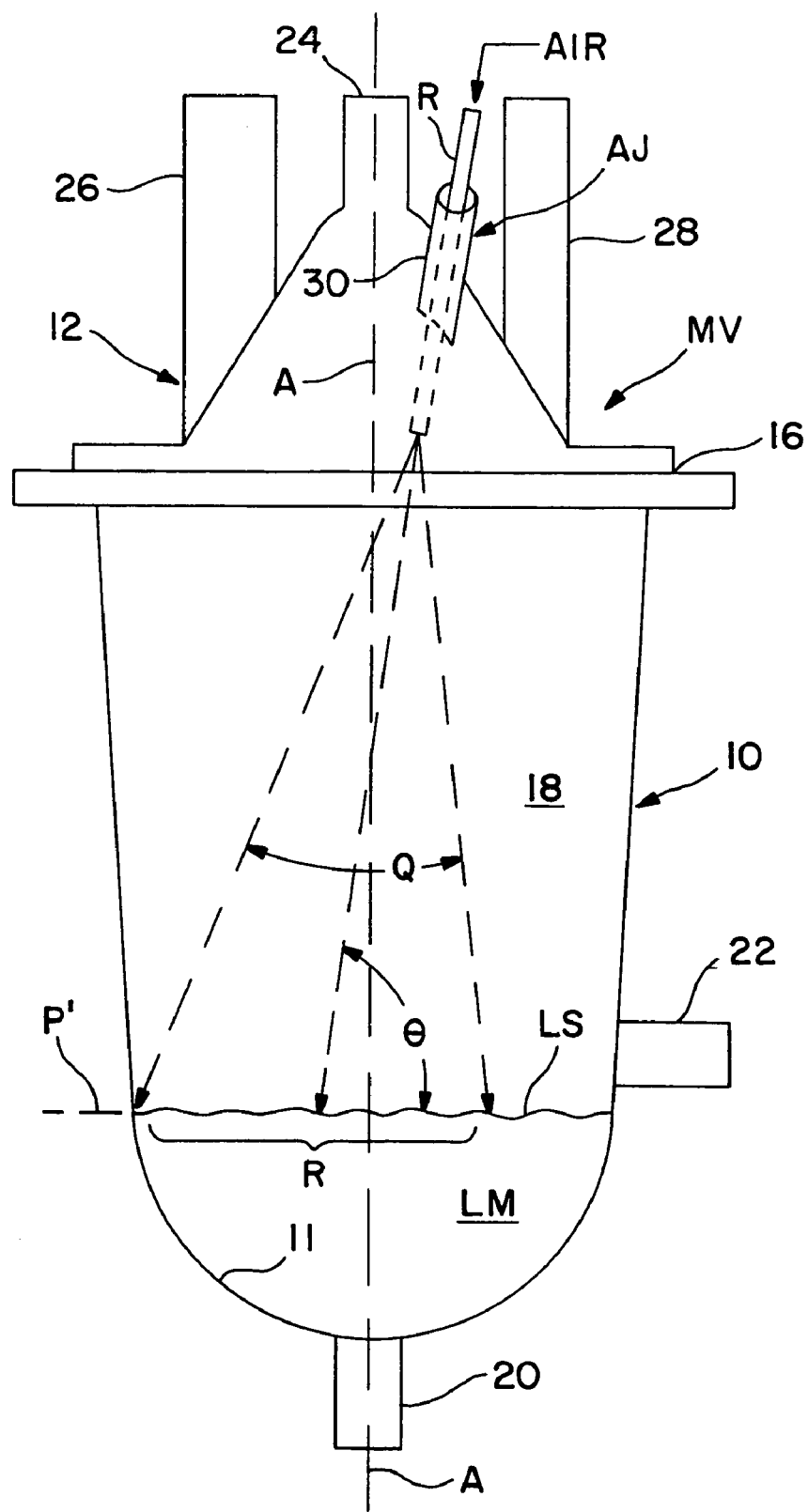
FIG. 2 is an enlarged illustration of one of the blood/reagent mixing vessels of the type used in the instruments of FIGS. 1A and 1B.
Figure 3A:
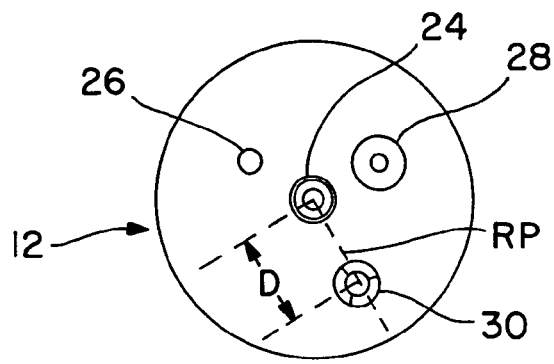
FIGS. 3A, 3B and 3C are top, side, and cross-sectional illustrations, respectively, of the cap portion of a mixing vessel of the type used in the FIGS. 1A and 1B instruments.
Figure 3B:
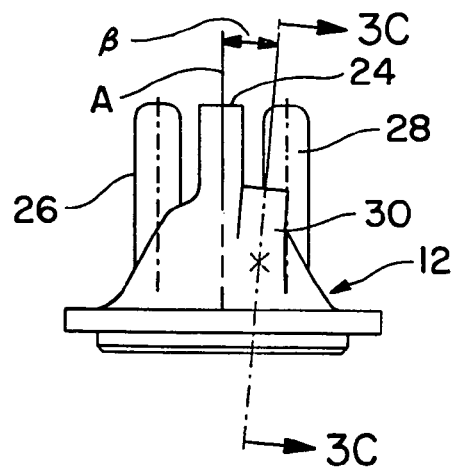
Figure 3C:
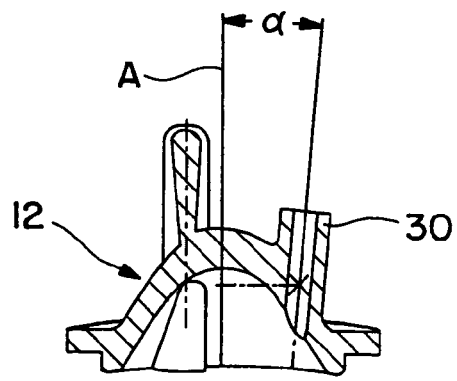

As best shown in the enlarged view of FIG. 2, each of the mixing vessels MV1-MV4 comprises a cup portion 10 and a cap portion 12. Preferably, both portions are injection molded from a transparent plastic, and the two portions are permanently sealed at the interface 16 defined by their respective rims. Cup portion 10 defines a smooth, concave surface 11 that serves as the liquid-supporting portion of an internal mixing chamber 18 for receiving and supporting the liquid material(s) LM to be mixed. An exit port 20 is provided at the base of the cup portion for extracting the liquid mixture from the mixing chamber after mixing is complete. Optionally, the cup portion may comprise an entry port 22 in the wall thereof, at a level above the anticipated level of the materials to be mixed. Such port is used to introduce the quench reagent used for a white cell analysis. Referring also to FIGS. 3A-3C, the cap portion of the mixing vessel is provided with two or more ports 24, 26 through which the sample liquid and reagent and/or diluent can enter the vessel for mixing. A third port 28 serves to vent the mixing chamber to the atmosphere.

In accordance with one aspect of the present invention, the cap portion 12 of each of the blood-mixings vessels described above is provided with a port 30 that is designed to support one or more of the above-mentioned air jets AJ used to mix the liquid contents of a mixing vessel. Each of the air jets preferably comprises a thin, hollow reed R having an outside diameter of, say, 1 or 2 mm, and an inside diameter of between about 0.1 and 1.0 mm., most preferably about 0.5 mm. The air jet reed may be made of plastic or metal. The length of the reed is not critical and may, for example, vary between about 10 and 50 mm. Depending on the type of cells being analyzed, the end of the air jet within the mixing vessel may be positioned between about 5 and 25 mm above the surface of the liquid in the mixing chamber. Preferably, the air jet reed passes through the cap portion of the mixing vessel about midway between the vessel axis A, extending vertically through the center of the mixing vessel and normal to the liquid contained thereby, and the mixing chamber rim defined by the cap/cup interface 16. The orientation of the reed within the vessel cap portion 12 depends on the type of cellular analysis to be performed. Generally, white cells are considerably more fragile than red cells and reticulocytes and, hence, must be mixed with more care and gentleness. Thus, the air jet is oriented to cause both a swirling and gentle tumbling of the cells in the mixture. This motion can be achieved by positioning the reed in an orientation so as to direct its associated air stream at two, relatively steep angles. Referring to FIGS. 3A-3C, it is apparent that the air jet reed R passes through the vessel cap 12 at a location displaced by a distance D, measured from the central vessel axis A in a radial plane RP containing axis A. Further, the reed axis is inclined in plane RP at a first angle $\alpha$ relative to the vessel axis A, and at a second angle $\beta$ measured in a plane perpendicular to the plane in which the first angle $\alpha$ is measured, i.e., perpendicular to the radial plane RP. Notice, the cross-sectional view of FIG. 3C is taken along the section line 3C-3C of FIG. 2. Preferably, angle $\alpha$ is between 2 and 6 degrees, and angle $\beta$ is between 4 and 10 degrees. Inclining the air jet at angle $\alpha$ causes the liquid in the chamber to gently tumble or churn. Inclining the air jet at angle $\beta$ causes the mixture to swirl, or rotate about the vessel axis A.

Referring again to FIG. 2, it is apparent that the center of the air stream S strikes the liquid surface LS at a relatively steep angle $\Theta$ measured with respect to the nominal plane P' of the liquid in the mixing vessel. Note, the air stream emerging from the end of reed R within the mixing chamber is not a narrow pencil of air; rather, it emerges from the end of reed R as a relatively broad cone of air, and the cone angle Q is determined by the applied pressure, the greater the pressure, the smaller the cone angle. Thus, the air stream striking the liquid surface in the vessel impinges the liquid over a relatively broad circular region R, the center of such area being offset from the center of the vessel, as shown in FIG. 2. This offset, together with the two angles of inclination, are instrumental in achieving, within a matter of seconds, excellent mixing of lysed and quenched mixtures. Most importantly, the integrity and population of the white blood cells sample are maintained throughout the mixing process.

To determine the effectiveness of the air-jet mixing method of the invention compared to the conventional orbital mixing method, a lysed blood sample was prepared from the same whole blood sample using the orbital mixing scheme of the prior art and the air jet mixing method of the invention. The two lysed samples, as produced by first mixing the blood sample with a lytic reagent, and then mixing the lysed sample with a lyse-quenching reagent, were processed by the same optical flow cell in a Gen*S™ hematology instrument made by Beckman Coulter, Inc. The best results in terms of the number of white cells counted per microliter of sample, were attained in the air jet mixing method when the angles $\alpha$ and $\beta$ were set at 6 and 2 degrees, respectively, the air pressure was approximately 5 PSI, and the spacing between the air jet end and the liquid surface was about 10 mm. The results showed that the white cell count was virtually identical for the two mixing methods. The comparative testing was repeated many times and, surprisingly, the air jet mixing method often resulted in a slightly greater count of white cells than did the conventional orbital mixing scheme incorporated in the Gen*S instrument. Thus, the blood sample-preparation method of the invention is highly advantageous in that the apparatus for implementing the method is very simple, i.e. a source of compressed air and an air jet suitably mounted in the cap of the mixing vessel, and the need for a relatively complex and costly orbital mixing apparatus is avoided.

In the case of providing a blood sample mixture that is suitable for red blood cell and reticulocyte analysis in the above-noted Gen*S instrument, it has been found that the requisite homogeneous mixing without cell damage can be achieved in a matter of a few seconds by directing the air stream in a direction substantially normal to the surface of the liquid in the vessel. In such case, angles α and β are both zero degrees. The desired tumbling action of the cells is increased due to the smaller angle α (compared to the 2-4 degrees used to prepare the white cell sample), and the swirling action is minimized, due to the smaller angle β (compared to the 5-10 degrees used in preparing the white cell sample).

Figure 4:
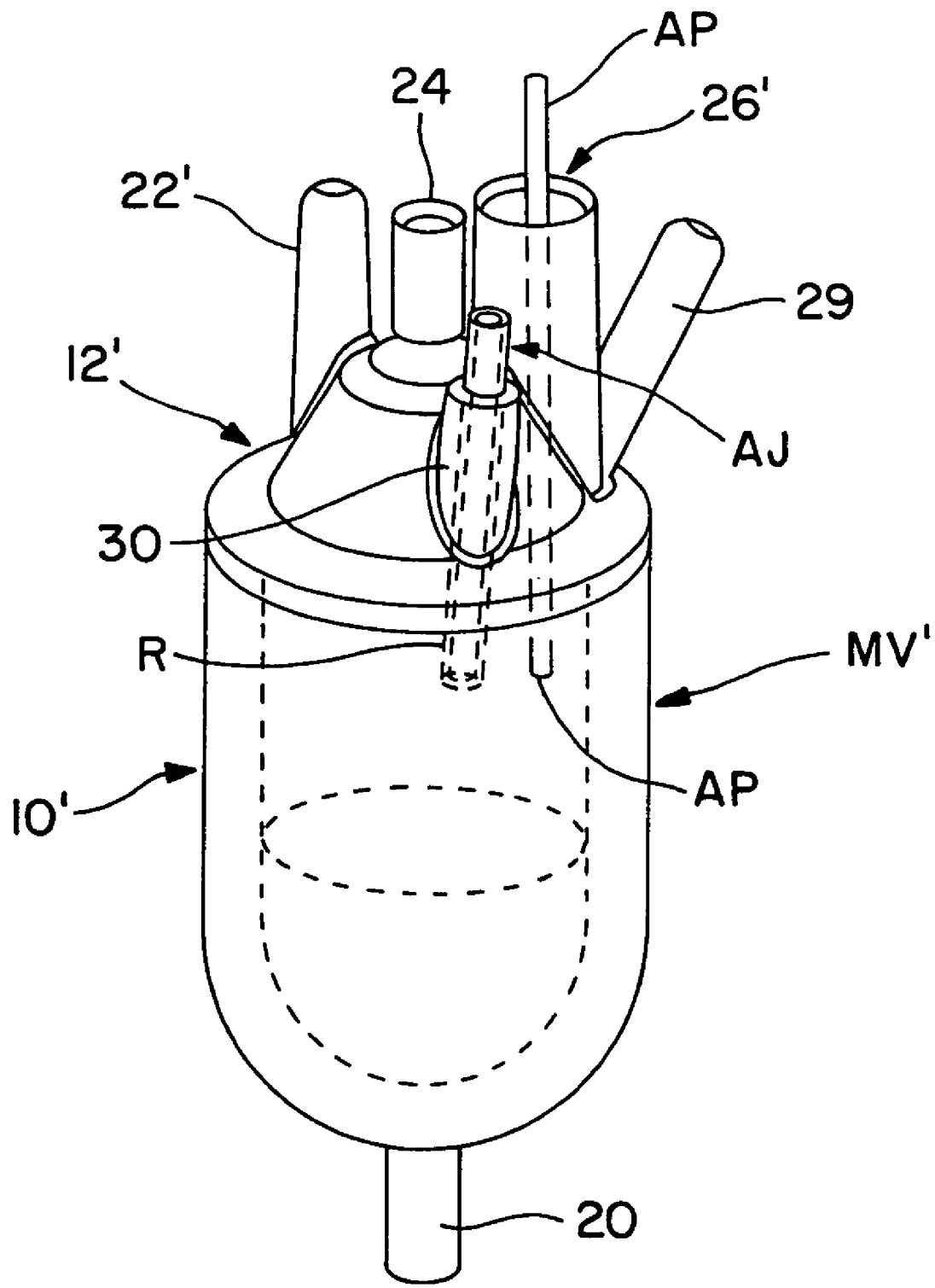
FIG. 4 is a perspective view of an alternative embodiment of the mixing vessel of the invention.

In FIG. 4, another preferred mixing vessel MV' embodying the present invention is shown. This mixing vessel is particularly adapted for use in preparing a blood sample for white cell analysis in a hematology instrument of the type in which a movably mounted probe or needle operates to both aspirate and dispense a blood sample. In this instrument, the probe is first caused to enter the sample-containing vial and to aspirate a portion of the sample. The probe is then moved to a mixing vessel where it is caused to enter the vessel and dispense all or a portion of the aspirated sample. As shown in FIG. 4, mixing vessel MV' comprises a multi-port cap portion 12' that is sealed to the top rim of a cup portion 10'. Port 26' is sized to receive the aspiration/dispense probe AP and to position the probe in a location extending into the internal volume of the cup portion 10' during the sample dispensing operation. Port 26' also serves as a vent port for the air jet pressure within the mixing vessel. In further contrast with the mixing vessel shown in FIG. 2, the quench port 22 formed in the cup portion 10 is now positioned in the cap portion 12' as port 22', and a separate lyse port 29 is provided. Preferably, the lyse port is angularly disposed relative to the sample port 26, whereby any blood sample remaining on the outer surface of the aspiration/dispense probe is washed therefrom by the lyse entering the mixing chamber through port 29. Air jet 30 is positioned in cap portion 12' as described above.

While the invention has been described with particular reference to preferred embodiments, it will be understood that variations can be made without departing from the spirit of the invention, and such variations are intended to fall within the scope of the appended claims. While the reagent is typically in the form of a liquid that is miscible with the blood sample, the reagent may comprise be in a powdered form.

What is claimed is:

1. A method for preparing a sample of whole blood for blood cell analysis in a hematology instrument in which a characteristic morphology of individual cell types is sensed by such instrument to differentiate one cell type from another in the whole blood sample, said method comprising the steps of:
   (a) dispensing predetermined volumes of whole blood and reagent material in a mixing chamber; and
   (b) mixing said volumes together by injecting a stream of air under pressure at the top surface of the contained volumes for a time and at a pressure sufficient to produce a homogeneous mixture containing blood cells having a characteristic morphology after the mixing step, said air stream being directed at the surface of materials within the mixing chamber at an angle of less than about 10 degrees measured with respect to a normal to said surface and at a region offset from the center of the mixing chamber.

2. The method as defined by claim 1 wherein said air stream is applied at a pressure not greater than 10 pounds per square inch and from a distance between 2 and 20 mm.

3. A method for preparing a sample of whole blood for white cell analysis in a hematology instrument which operates to differentiate different types of blood cells on the basis of a characteristic morphology of different cell types, said method comprising the steps of:
   (a) dispensing predetermined volumes of whole blood and reagent material in a mixing chamber; and
   (b) mixing said volumes together by injecting a stream of air under pressure at the top surface of the contained volumes for a time sufficient and at a pressure sufficient to produce a homogeneous mixture containing blood cells having a characteristic morphology after the mixing step, said air stream being directed at said top surface at a region offset from the center of the mixing chamber and at a first angle of less than about 6 degrees measured with respect to a normal to said top surface and in a radial plane containing the central longitudinal axis of said mixing chamber, and at a second angle of not greater than about 10 degrees measured in a plane normal to said radial plane.

4. The method as defined by claim 3 wherein said first angle is about 2 degrees, and wherein said second angle is about 6 degrees.

5. The method as defined by claim 3 wherein said air stream is applied at a pressure not greater than 10 pounds per square inch from a distance between 2 and 20 mm.

6. The method as defined by claim 5 wherein said air stream pressure is about 5 pounds per square inch.

7. The method as defined by claim 1 wherein said reaction vessel comprises (i) a cup portion including a housing defining a mixing chamber for receiving and supporting said predetermined volumes of blood and reagent material; and (ii) a cap portion sealable with said cup portion to enclose said mixing chamber, said cap portion having at least a first port for admitting said predetermined volumes of blood and reagent material to said mixing chamber for mixing, and a second port supporting a rectilinear tube through which said air stream can be directed at said angle and at said region of the surface of the materials within said mixing chamber.

8. The method as defined by claim 7 wherein said first port is adapted to receive a blood-dispensing probe by which a blood sample can be dispensed into said mixing chamber, and wherein cap portion has a third port formed therein through which a reagent liquid can be directed at said probe while said probe is received by said first port for the purpose of cleansing said probe.

9. The method as defined by claim 8 wherein said third port is angularly disposed with respect to said first port.

* * * * *